United States Patent
Rodgers et al.

(10) Patent No.: US 10,195,282 B2
(45) Date of Patent: Feb. 5, 2019

(54) USE OF ALGINATE FORMULATION FOR INTRAINCISIONAL DRUG DELIVERY

(71) Applicant: UNIVERSITY OF SOUTHERN CALIFORNIA, Los Angeles, CA (US)

(72) Inventors: Kathleen E. Rodgers, Los Angeles, CA (US); Kevin J. Gaffney, Los Angeles, CA (US); Gere S. Dizerega, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 15/527,541

(22) PCT Filed: Nov. 20, 2015

(86) PCT No.: PCT/US2015/061808
§ 371 (c)(1),
(2) Date: May 17, 2017

(87) PCT Pub. No.: WO2016/081820
PCT Pub. Date: May 26, 2016

(65) Prior Publication Data
US 2017/0354736 A1 Dec. 14, 2017

Related U.S. Application Data

(60) Provisional application No. 62/082,214, filed on Nov. 20, 2014.

(51) Int. Cl.
*A61K 38/08* (2006.01)
*A61K 47/36* (2006.01)
*A61L 26/00* (2006.01)
*A61K 9/00* (2006.01)

(52) U.S. Cl.
CPC ............ *A61K 47/36* (2013.01); *A61K 9/0014* (2013.01); *A61K 38/08* (2013.01); *A61L 26/008* (2013.01); *A61L 26/009* (2013.01); *A61L 26/0023* (2013.01); *A61L 26/0061* (2013.01); *A61L 26/0066* (2013.01); *A61L 2300/232* (2013.01); *A61L 2400/06* (2013.01)

(58) Field of Classification Search
CPC .. A61K 9/0014; A61K 9/0019; A61K 9/0024; A61K 38/08; A61K 38/085; A61K 47/36; A61L 15/28; A61L 26/0023; A61L 2300/232

See application file for complete search history.

(56) References Cited

U.S. PATENT DOCUMENTS

| 2005/0137272 A1 | 6/2005 | Gaserod et al. | |
| 2006/0051431 A1* | 3/2006 | Becker | A61K 33/38 424/618 |
| 2006/0212055 A1* | 9/2006 | Karabey | A61B 17/12022 606/158 |
| 2009/0074908 A1 | 3/2009 | Rompala | |
| 2011/0257504 A1* | 10/2011 | Hendricks | A61B 5/0408 600/395 |

FOREIGN PATENT DOCUMENTS

| CN | 102532564 B * | 9/2013 | ......... C08B 37/0084 |
| EP | 0 380 253 A2 | 8/1990 | |
| GB | 2 322 864 A | 9/1998 | |
| GB | 2 490 516 A | 11/2012 | |
| WO | 2003/087303 A2 | 10/2003 | |

OTHER PUBLICATIONS

K E Rodgers et al. "Fragments of Nle 3-angiotensin(1-7) accelerate healing in dermal models", J. Peptide Res. (2006) Copyright Blackwell Munksgaard, pp. 41-47, XP055243485, Retrieved from the Internet: URL:http://onlinelibrary.wiley.com/doi/10.1111/j.1747-0285.2006.00350.x/epdf.
The International Search Report (ISR) with Written Opinion for PCT/US2015/061808 dated Feb. 2, 2016, pp. 1-18.

* cited by examiner

*Primary Examiner* — Jeffrey E. Russel
(74) *Attorney, Agent, or Firm* — McDonnell Boehnen Hulbert & Berghoff LLP

(57) ABSTRACT

Described herein are compositions of alginate formulations that include water, divalent ions, and alginate cross-linked by the divalent ions, and their use for treating incisional wounds, such as intra-incisional application.

17 Claims, 5 Drawing Sheets
Specification includes a Sequence Listing.

USE OF ALGINATE FORMULATION FOR INTRAINCISIONAL DRUG DELIVERY

CROSS REFERENCE

This application is a U.S. national phase of International Application No. PCT/US2015/061808, filed on Nov. 20, 2015, which claims priority to U.S. Provisional Application No. 62/082,214, filed Nov. 20, 2014, both of which are incorporated by reference herein in their entirety.

BACKGROUND

Alginates comprise a rather broad family of polysaccharides capable of forming soft hydrogels that are found in brown seaweeds with certain varieties of different alginates being produced by bacteria. Appropriate use of intra-incisional formulations requires that the material stay the appropriate period of time for the necessary efficacy and to be safe for use (non-inflammatory, does not interfere with tissue healing). These demands are quite stringent and limit the utility of a number of materials.

DETAILED DESCRIPTION OF THE INVENTION

Figure 1:
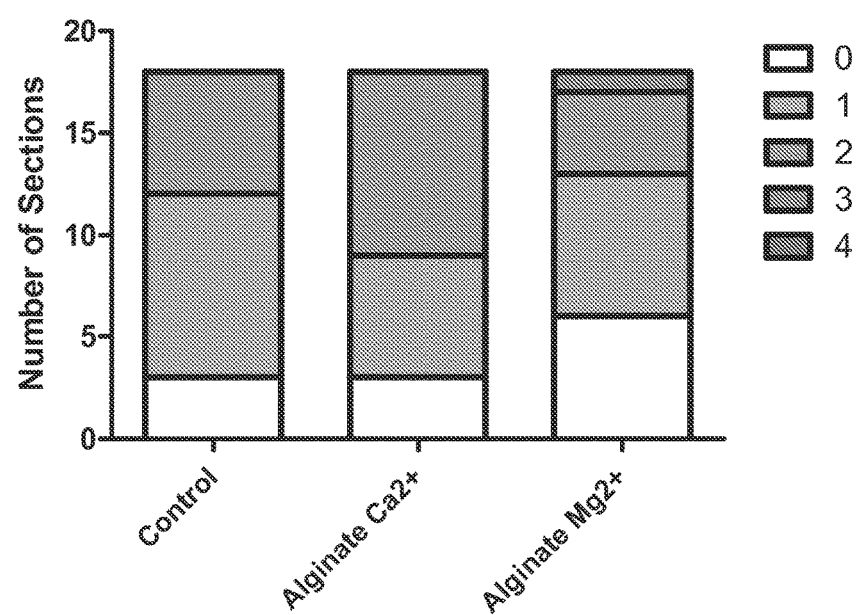
FIG. 1 is a graph of results demonstrating properties of different ionic cross linked alginates and numbers of sections according to cellular scoring index when compared to control.

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* $22^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* $3^{rd}$ ed., revised ed., J. Wiley Sons (New York, N.Y. 2006); Smith, *March's Advanced Organic Chemistry Reactions, Mechanisms and Structure* $7^{th}$ ed., J. Wiley & Sons (New York, N.Y. 2013); Singleton, *Dictionary of DNA and Genome Technology* $3^{rd}$ ed., Wiley-Blackwell (Nov. 28, 2012); and Green and Sambrook, *Molecular Cloning: A Laboratory Manual 4th ed.*, Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* $2^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

As used herein, the term "about" means +/−5% of the recited parameter.

Described herein is a composition comprising water, divalent ions; and between about 0.5% to about 10% alginate, wherein the alginate is cross-linked via the divalent ions. As disclosed herein, the compositions can be used, for example, in incisional wound healing.

Alginates are co-polymer mixtures of poly(mannuronic acid) with 13-1,4-linked mannuronic acid residues (abbreviated M) combined with C5-epimer, c-L-guluronic acid (abbreviated G) that are strictly linear, unbranched structures. The content of G in major algal alginates varies roughly between 40% and 70%. At physiological conditions, alginate forms hydrogels. Mixture of sodium alginate of high molecular weight and dripping into a solution of calcium immediately spurs the cross-linking of alginate strands by calcium. Alginate has a high affinity towards calcium, and calcium binds consecutive G-residues (G-blocks) in different alginate chains in a cooperative manner, thereby producing the crosslinks of the hydrogel. Binding of divalent cations, such as calcium to the guluronic residues in adjacent alginate chains allows formation of an "egg-box" structure across polymer strands. Gelation can also occur by incorporating magnesium. MG-blocks also participate in the formation of crosslinks with calcium, participating in the crosslinking of MG-blocks in two alginate chains as well as MG-blocks in one chain and G-blocks in another chain. Crosslinking affects the resulting gel properties, such as stiffness, elasticity, syneresis and stability.

In various embodiments, the composition is between about 0.5% to about 10% alginate, about 0.5% to about 9% alginate, about 0.5% to about 8% alginate, about 0.5% to about 7% alginate, about 0.5% to about 6% alginate, about 0.5% to about 5% alginate, about 0.5% to about 0.5% alginate, about 0.5% to about 3% alginate, about 0.5% to about 2.5% alginate, about 1% to about 10% alginate, about 1% to about 9% alginate, about 1% to about 8% alginate, about 1% to about 7% alginate, about 1% to about 6% alginate, about 1% to about 5% alginate, about 1% to about 4% alginate, about 1% to about 3% alginate, about 1% to about 2.5% alginate, about 2% to about 10% alginate, about 2% to about 9% alginate, about 2% to about 8% alginate, about 2% to about 7% alginate, about 2% to about 6% alginate, about 2% to about 5% alginate, about 2% to about 4% alginate, about 2% to about 3% alginate, about 2% to about 2.5% alginate, 0.25% to 0.5% alginate, about 0.5-1.0% alginate, about 1.0-1.5% alginate, about 1.5-2.0% alginate, about 2.0-2.5% alginate, about 2.5-3.0% alginate, about 3.0-3.5% alginate, about 3.5-4.0% alginate, about 4.0-4.5% alginate, about 4.5-5% alginate, about 5-5.5% alginate, and 5.5% or more alginate, such as 5.5% to 10%. In various embodiments, the divalent ion is calcium or magnesium. In various embodiments, the calcium ion concentration is about 0.5-1 mM, about 1-1.5 mM, about 1.5-2.0 mM, about 2.0-2.5 mM, about 2.5-3 mM, about 3-3.5 mM, about 3.5-4.0 mM, about 4.0-4.5 mM, about 4.5-5 mM, about 5-5.5 mM, and 5.5 mM or more, such as 5.5 mM to 10 mM. In various embodiments, the magnesium ion concentration is about 5-10 mM, about 10-15 mM, about 15-20 mM, about 20-25 mM, about 25-30 mM, about 30-35 mM, about 35-40 mM, about 40-45 mM, about 45-50 mM, about 50-55 mM, and 55 mM or more, such as 55 mM to 100 mM, and alginate, wherein the ratio of sodium ions to calcium ions is between about 15:1 to about 45:1, and the amount of alginate is between about 0.3 and 4%, preferably about 0.7 and 2%. In various embodiments, the alginate includes a buffer, such as phosphate buffer, at concentrations of about 0.001 M, about 0.002 M, about 0.003 M, about 0.004 M, about 0.005 M about 0.006 M, about 0.007 M, about 0.008 M about 0.009 M, about 0.010 M or more. In various embodiments, the alginate includes a G-content of about 30%, about 40%, about 50%, about 60%, about 70% or more (wherein M content would then be about 70%, about 60%, about 50%, about 40%, or about 30%, respectively). In other embodiments, M-content is less than about 70%, about 80%, about 90%, about 95%, about 97%, about 99%, with corresponding G content adding to 100%. Any suitable molecular weight of alginate can be used. In one embodiment, the alginate molecular weight is between about 10 kDa and about 250 kDa. In various further embodiments, the alginate molecular weight is between about 50 kDa and about 250 kDA, about 70 kDa and about 250 kDa, about 100 kDa and about 250 kDa, about 125 kDa and about 250 kDa, about 150 kDa and about 250 kDa, 50 kDa, and about 200 kDA, about 70 kDa and about 200 kDa, about 100 kDa and about 200 kDa, about 125 kDa and about 200 kDa, or about 150 kDa and about 200 kDa. In various further embodiments, the alginate molecular weight is about. In various embodiments, the composition includes water, 1-10 of calcium ion, and 1-5% alginate. In other embodiments, the composition includes water, about 5 mM of calcium ion and about 2.5% alginate. In various embodiments, the composition includes water, 10-100 mM of magnesium ion, and between about 1% to about 7% alginate. In other embodiments, the composition includes water, about 50 mM of magnesium ion and about 4% alginate. In various embodiments, the composition includes 0.001-0.010 M phosphate buffer, such as 0.005 M phosphate buffer.

Further described herein s a composition including water, a divalent ion, and alginate further coupled with a therapeutic agent. Examples of therapeutic agents include a peptide, protein, antibody, nucleic acid, small molecule drug. For example, peptides, proteins, and/or antibody can be covalently coupled to alginate in the composition. In other examples, nucleic acids may include antisense nucleic acids or small interfering RNAs (siRNAs). In other embodiments, small molecules may be infused in the alginate copolymer.

In one embodiment, the therapeutic agent comprises or consists of at least 5 amino acids of Nle3A(1-7) (or Nor-Leu$^3$-A(1-7)), or a pharmaceutically acceptable salt thereof. Nle3A(1-7) is a peptide consisting of the amino acid sequence Asp-Arg-Nle-Tyr-Ile-His-Pro (SEQ ID NO:1). In various embodiments, the peptide administered to the subject may comprise or consist of Asp-Ara-Me-Tyr-He (SEQ ID NO:2), Asp-Arg-Nle-Tyr-Ile-His (SEQ ID NO:3), or most preferably Asp-Arg-Nle-Tyr-Ile-His-Pro (SEQ ID NO:1), or salts thereof. Nle3A(1-7) or salts thereof may be chemically synthesized or recombinantly expressed, each of which can be accomplished using standard methods in the art.

In one embodiment, the peptide, or salt thereof, is present in the composition at a concentration of about 0.001% to about 3% on a weight (mg)/volume (ml) basis, or on a weight/weight (mg) basis. 0.03% to about 1% on a weight (mg)/volume (ml) basis, or on a weight/weight (mg) basis. In various further embodiments, the peptide, or salt thereof, is administered at a concentration of about 0.001% to about 2%, about 0.001% to about 1%, about 0.005% to about 3%, about 0.005% to about 2%, about 0.005% to about 1%, about 0.0075% to about 3%, about 0.0075% to about 2%, about 0.0075% to about 1%; about 0.01% to about 3%, about 0.01% to about 2%, about 0.01% to about 1%, about 0.03% to about 3%, about 0.03% to about 2%, about 0.03% to about 1%, about 0.03% to about 0.75%; about 0.03% to about 0.5%; about 0.03% to about 0.25%; about 0.03% to about 0.1%; about 0.03% to about 0.075%; about 0.03% to about 0.05%; and about 0.03%; all on a weight (mg)/volume (ml) basis, or on a weight/weight (mg) basis.

Also described herein, the present invention composition including methods for treating an incisional wound comprising:

administering a composition comprising water, divalent ions, and alginate cross-linked by the divalent ions, to an incisional wound in a subject for a time and in an amount effective to treat the incisional wound.

As described in the examples that follow, the inventors have surprisingly discovered that the compositions and methods of the invention result in reduced scarring at the site of a incisional wound compared to the use of other formulations. As used herein an "incisional wound" is a laceration (i.e.: cut), abrasions, burns, or opening in the skin. The methods can be used at any suitable incisional wound, including but not limited to an open surgical incision in the subject or an incision caused by trauma, to the subject. The inventors have further surprisingly discovered that the compositions and methods of the invention reduce dehiscence compared to control following closing of the incisional wound (such as a surgical incision). This is unexpected, as those of skill in the art would expect the use of a foreign body, such as the compositions of the invention, to increase dehiscence as a result of tissue-tissue contact.

As used herein, "treating" an incisional wound includes
(a) limiting the progression in size, area, and/or depth of the incisional wound;
(b) reducing size, area, and/or depth of the incisional wound;
(c) increasing rate of healing and/or reducing time to healing;
(d) decreasing scarring from the wound/wound closure relative to control (i.e.: no treatment or standard or care treatment); and
(e) decreased dehiscence relative to control after wound closure.

The methods can be used to reducing scarring and/or dehiscence following closing of the wound associated with any type of surgical procedure. In various non-limiting embodiments, the incisional wound is associated with abdominal surgery, cosmetic surgery, reconstructive surgery, oral surgery, scar revision, gynecological surgery, thoracic surgery, orthopedic surgery, wart ablation, neurological surgery, laminectomies, discectomies, arthroscopic surgery, breast augmentation surgery, child birth, and joint replacement surgery. In further embodiments, the methods can be used to reduce scarring and/or dehiscence following closing of an incisional wound caused by any type of trauma, including but not limited to anal or vaginal fissures; rectal fistulas; anal, vaginal, nasal, or ear incisional wounds due to mechanical, percussive, foreign body or chemical injury, incisional wounds to the epithelial layer covering the ear drum (including incisional wounds caused by inner ear infections or any other trauma), and incisional wounds to the urethra. In a further embodiment, the methods comprise closing the incision; in this embodiment, the composition may be retained at the incision site at the time of closure, which can be any suitable method including suturing, bonding, sealing etc.

The subject may be any suitable subject, including mammals such as humans.

The methods can be carried out using an embodiment or combination of embodiments of the compositions of the invention. In various exemplary embodiments (which may be combined unless the context clearly dictates otherwise)), the composition comprises the between about 1% to about 10% alginate; the divalent ions comprises calcium ions at a concentration of between about 1 mM and about 10 mM; the calcium ion concentration is about 5 mM; the divalent ions comprise magnesium ions at a concentration of between about 10 nM and about 100 mM; the magnesium ion concentration is about 50 mM; the alginate concentration is between about 2% and about 4%; wherein the alginate concentration is between about 2% and about 2.5%; the composition further comprises between about 0.001 M and about 0.010 M phosphate buffer; and/or the phosphate buffer is present at a concentration of about 0.005 M.

In a further embodiment of the methods of the invention, the composition further comprises a therapeutic agent. Any therapeutic agent suitable for use in treating a wound may be used. Examples of therapeutic agents include a peptide, protein, antibody, nucleic acid, small molecule drug, or an antibiotic. For example, peptides, proteins, and/or antibody can be covalently coupled to alginate in the composition. In other examples, nucleic acids may include antisense nucleic acids or small interfering RNAs (siRNAs). In other embodiments, small molecules may be infused in the alginate copolymer.

In one embodiment, the therapeutic agent comprises or consists of at least 5 amino acids of Nle3A(1-7) (or Nor-Leu$^3$-A(1-7))), or a pharmaceutically acceptable salt thereof. In various embodiments, the peptide administered to the subject may comprise or consist of Asp-Arg-Nle-Tyr-Ile (SEQ ID NO:2), Asp-Arg-Nle-Tyr-Ile-His (SEQ ID NO:3), or most preferably Asp-Arg-Nle-Tyr-Ile-His-Pro (SEQ ID NO:1), or salts thereof. Nle3A(1-7) or salts thereof may be chemically synthesized or recombinantly expressed, each of which can be accomplished using standard methods in the art.

In one embodiment, the peptide, or salt thereof, is present in the composition at a concentration of about 0.001% to about 1% on a weight (mg)/volume (ml) basis, or on a weight/weight (mg) basis. 0.03% to about 1% on a weight (mg)/volume (ml) basis, or on a weight/weight (mg) basis. In various further embodiments, the peptide, or salt thereof, is administered at a concentration of about 0.005% to about 1%, 0.0075% to about 1%; 0.01% to about 1%, 0.03% to about 1%, 0.03% to about 0.75%; about 0.03% to about 0.5%; about 0.03% to about 0.25%; about 0.03% to about 0.1%; about 0.03% to about 0.075%; about 0.03% to about 0.05%; and about 0.03%; all on a weight (mg)/volume (ml) basis, or on a weight/weight (mg) basis.

The composition is administered via topical administration. In one embodiment, the methods of the invention can comprise topically administering the composition as often as deemed appropriate, ie: once per day, twice per day, etc. The methods may further comprise administration of the composition for as longed as deemed desirable by an attending physician, for example, until healing of the incisional wound. For administration, it is preferred that the topical composition form a continuous film covering the entire area of the incisional wound, including the margins. In a preferred embodiment, the topical composition is applied with a thickness of approximately 0.25 to 2 mm; preferably 0.5 to 1.5 mm; preferably about 1 mm in thickness.

The composition may be administered together with one or more (a) a lyoprotectant; (b) a surfactant; (c) a bulking agent; (d) a tonicity adjusting agent; (e) a stabilizer; (f) a preservative and/or (g) a buffer. In some embodiments, the buffer in the pharmaceutical composition is a Tris buffer, a histidine buffer, a phosphate buffer, a citrate buffer or an acetate buffer. The composition may be administered with a lyoprotectant, e.g. sucrose, sorbitol or trehalose. In certain embodiments, the composition may be administered with a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the composition may be administered with a bulking agent, like glycine. In yet other embodiments, the therapeutic may be administered with a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The composition may be administered with a tonicity adjusting agent, e.g., a compound that renders the composition substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the composition may be administered with a stabilizer, e.g., a molecule which, when combined with the peptide substantially prevents or reduces chemical and/or physical instability of the therapeutic (when present). Exemplary stabilizers include sucrose, sorbitol, glycine, inositol, sodium chloride, methionine, arginine, and arginine hydrochloride, paraben, and combinations of methyl paraben and propyl paraben.

In all aspects and embodiments of the invention, suitable acids which are capable of forming salts with the therapeutic include, but are not limited to, inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid and the like. Suitable bases capable of forming salts with the therapeutic include, but are not limited to, inorganic bases such as sodium hydroxide, ammonium hydroxide, potassium hydroxide and the like; and organic bases such as mono-, di- and tri-alkyl and aryl amities (e.g., triethylamine, diisopropyl amine, methyl amine, dimethyl amine and the like) and optionally substituted ethanolamines (e.g., ethanolamine, diethanolamine and the like).

The peptide therapeutic or salt thereof can further be derivatized to provide enhanced half-life, for example, by linking to polyethylene glycol. The peptide therapeutic or salt thereof may comprise L-amino acids, D-amino acids (which are resistant to L-amino acid-specific proteases in vivo), a combination of D- and L-amino acids, and various "designer" amino acids (e.g., β-methyl amino acids, Cα-methyl amino acids, and Nα-methyl amino acids, etc.) to convey special properties.

The peptide therapeutic or salt thereof may be the sole active agent in the pharmaceutical composition, or the composition may further comprise one or more other active agents suitable treating a incisional wound, such as an antibiotic, an anti-inflammatory therapeutic, growth factor, stem cells, anti-parasitics, anti-virals, immune suppressants/modulators, and/or analgesics. Exemplary other therapeutics that can be used in the compositions, with or without Nle3A(1-7) include:

Antibiotics
  Penicillins including, but not limited to Amoxicillin, Ampicillin, Bacampicillin, Carbenicillin, Cloxacillin, Dicloxacillin, Flucloxacillin, Mezlocillin, Nafcillin, Oxacillin, Penicillin G, Penicillin V, Pipera-cillin, Pivampicillin, Pivmecillinam, Ticarcillin);
  Cephalosporins including, but not limited to Cefacetrile (cephacetrile), Cefadroxil (cefadroxyl), Cefalexin (cephalexin), Cefaloglycin (cephaloglycin), Cefalonium (cephalonium), Cefaloridine (cephaloridine), Cefalotin (cephalothin), Cefapirin (cephapirin), Cefatrizine, Cefazaflur, Cefazedone, Cefazolin (cephazolin), Cefradine (cephradine), Cefroxadine, Ceftezole, Cefaclor, Cefamandole, Cefmetazole, Cefonicid, Cefotetan, Cefoxitin, Cefprozil (cefproxil), Cefuroxime, Cefuzonam, Cefcapene, Cefdaloxime, Cefdinir, Cefditoren, Cefetamet, Cefixime, Cefmenoxime, Cefodizime, Cefotaxime, Cefpimizole, Cefpodoxime, Cefteram, Ceftibuten, Ceftiofur, Ceftiolene, Ceftizoxime, Ceftriaxone, Cefoperazone, Ceftazidime, Cefelidine, Cefepime, Cefluprenam, Cefoselis, Cefozopran, Cefpirome, Cefquinome, Ceftobiprole, Ceftaroline, Cefaclomezine, Cefaloram, Cefaparole, Cefcanel, Cefedrolor, Cefempidone, Cefetrizole, Cefivitril, Cefmatilen, Cefmepidium, Cefovecin, Cefoxazole, Cefrotil, Cefsumide, Cefuracetime, Ceftioxide;
  Monobactams including, but not limited to Aztreonam;
  Carbapenems including, but not limited to Imipenem, Imipenem/cilastatin, Doripenem, Meropenem, Ertapenem,
  Macrolide Antibiotics including, but not limited to Azithromycin, Erythromycin, Clarithromycin, Dirithromycin, Roxithromycin, Telithromycin;
  Lincosamides including, but not limited to Clindamycin, Lincomycin;
  Streptogramins including, but not limited to Pristinamycin, Quinupristin/dalfopristin;
  Aminoglycoside Antibiotics including, but not limited to Amikacin, Gentamicin, Kanamycin, Neomycin, Netilmicin, Paromomycin, Streptomycin, Tobramycin;
  Quinolone Antibiotics including, but not limited to: Flumequine, Nalidixic acid, Oxolinic acid, Piromidic acid, Pipemidic acid, Rosoxacin, Ciprofloxacin, Enoxacin, Lomefloxacin, Nadifloxacin, Norfloxacin, Ofloxacin, Pefloxacin, Rufloxacin, Balofloxacin, Gatifloxacin, Grepafloxacin, Levofloxacin, Moxifloxacin, Pazufloxacin, Sparfloxacin, Temafloxacin, Tosufloxacin, Besifloxaein, Clinafloxacin, Gemifloxacin, Sitafloxacin, Trovafloxacin, Prulifloxacin;
  Sulfonamides including, but not limited to Sulfamethizole, Sulfamethoxazole, Sulfisoxazole, Trimethoprim-Sulfamethmazole;
  Tetracycline Antibiotics including, but not limited to Demeclocycline, Doxycycline, Minocycline, Oxytetracycline, Tetracycline, Tigecycline;
  Glycopeptides including, but not limited to Vancomycin, Teicoplanin;
  Lipoglycopeptides including, but not limited to Telavancin;
  Oxazolidinones including, but not limited to Linezolid, Cycloserine;
  Rifamycins including, but not limited to Rifampin, Rifabutin, Rifapentine;
  Polypeptides including, but not limited to: Bacitracin, Polymyxin B;
  Tuberactinomycins including, but not limited to Viomycin, Capreomycin;
  Chloramphenicol, Metronidazole, Tinidazole, Nitrofurantoin, Lipopeptides, Fluoroquinolone, Lipoglycopeptides, Cephalosporin, Macrocyclics;
Anti-inflammatory drugs
  Non-Steroidal Anti-Inflammatory Drugs including, but not limited to acetylsalicylic acid, Bromfenac, Diclofenac, Diflunisal, Etodolac, Fenoprofen, Flurbiprofen, Ibuprofen, Indomethacin, Ketoprofen, Ketorolac, Meclofenamate, Mefenamic Acid, Meloxicain, Nabumetone, Naproxen, Oxaprozin, Phenylbutazone, Piroxicam, Sulindac, Tolmetin, VBP15;
  Glucocorticoids including, but not limited to cortisol, cortisone, prednisone, prednisolone, methylprednisolone, dexamethasone, betamethasone, triamcinolone, beclomethasone, aldosterone;
Anti-parasitic drugs
  Including, but not limited to Mebendazole, Pyrantel pamoate, Thiabendazole, Diethylcarbamazine, Ivermectin, Niclosamide, Praziquantel, Albendazole, Praziquantel, Rifampin, Amphotericin B, Melarsoprol, Eflomithine, Metronidazole, Tinidazole, Miltefosine;
Anti-viral drugs
  Including, but not limited to Abacavir, Aciclovir, Acyclovir, Adefovir, Amantadine, Amprenavir, Ampligen, Arbidol, Atazanavir, Atripla, Balavir, Cidofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fomvirsen, Fosamprenavir, Foscarnet, Fosfonet, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Novir, Oscltamivir, Peginterferon alfa-2a, Penciclovir, Peramivir, Pleconaril, Podophyllotoxin, Raltegravir, Ribavirin, Rimantadine, Ritonavir, Pyramidine, Saquinavir, Sofosbuvir, Stavudine, Telaprevir, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir (Relenza), Zidovudine Immune suppressants/modulators
  a Glucocorticoids including but not limited to cortisol, cortisone, prednisone, prednisolone, methylprednisolone, dexamethasone, betamethasone, triamcinolone, beclomethasone, aldosterone;
  Cytostatics including but not limited to alkylating agents (e.g. cyclophosphamide, nitrosoureas), antimetabolites (e.g. methotrexate, fluorocuracil);
  Immunophilin modulators including but not limited to ciclosporin, Tacrolimus, Sirolimus;
  Interferons including but not limited to interferon alpha 2a, Interferon alpha 2b, Human leukocyte Interferon-alpha (HuIFN-alpha-Le), Interferon beta 1a, Interferon beta 1b, Interferon gamma 1b, PEGylated interferon alpha 2a, PEGylated interferon alpha 2b;
  Sphingosine 1-phosphate receptor modulator including but not limited to fingolimod, Ozanimod;
  TNF-α (tumor necrosis factor-alpha) binding protein including but not limited to infliximab, etanercept, adalimumab;
  Mycophenolate;
Growth stimulating factors including hut not limited to Epidermal Growth Factor (EGF), Transforming Growth Factor, Vascular Endothelial Growth Factor (VEGF), Fibroblast Growth Factor (FGF), Platelet-Derived Growth Factor (PDGF), interleukins, Colony-stimulating factor, Keratinocyte growth factor;
Stem cells; and
Analgesics including but not limited to Buprenorphine, Butorphanol, Codeine, Hydrocodone, Hydromorphone, Levorphanol, Meperidine, Methadone, Morphine, Nalbuphine, Oxycodone, Oxymorphone, Pentazocine, Propoxyphene, Tapentadol, Tramadol, Tramadol and Acetaminophen, Capsaicin, Benzocaine, Benzocaine/Menthol, Dibucaine, Lidocaine, Lidocaine/Prilocaine.

Example 1

Protocol Design

A protocol was designed to evaluate the effect of administration of two formulations of alginate crosslinked with Ca2+ or Mg2+ in 0.005 M phosphate buffer, pH 6, on early inflammatory responses in full thickness incision wounds in a rat model. Female Sprague Dawley rats (n=3/group) were studied for appearance of healing wound and inflammation at the site of implantation. The test article included: 1) 0.005 M phosphate buffer, pH 6.0, 2) 2% Alginate (Spectrum 1BI0132, USBNF Grade, MW 222.0) crosslinked with 5 mM Ca2+, or 3) 4% Alginate crosslinked with 50 mM Ma2+

Alginate was prepared by using sterile snap top polypropylene tubes (10×13 mm) that were pre-weighed and an aliquot of alginate added per tube. The tube was then post-weighed and the amount of diluent (0.005 M phosphate buffer) added to make the percentage formulation listed above. 5 mM CaCl$_2$ or 50 mM MgCl$_2$ was then added to crosslink the alginate. The formulations were then placed in 1 mL syringes for delivery to the surgery room and use.

Thirty nine rats were used. During the experimental period, female, Sprague Dawley rats, 200-225 g, were housed one per cage and maintained in a central animal care facility with a 12-hour light/dark cycle. Water and standard rodent laboratory chow were supplied ad libitum.

On the dorsal surface of rats, two full thickness incisions (3 cm in length) were made on a prepared surface under aseptic conditions. After injury, exposure to 100 µl/wound of the formulation (3 rats, 6 incisions per formulation) was administered into the open incision wound prior to closure. The wound was then sutured closed.

The animals were monitored for breathing, urination and movement during the postoperative interval. Postoperative analgesic included twice daily administration of bupronex for 3 days postop. At various times after surgery, the rats was observed for the appearance of the healing wound. On days 7, the rats were euthanized by $CO_2$ asphyxiation and tissues harvested for histologic preparation.

The tissues were placed in formalin overnight to fix and then prepared for sectioning and staining. The tissues were stained with hematoxylin and eosin. The microscopic evaluation included the degree of inflammatory cell infiltration. The cellular index scoring was defined as shown in Table 1.

TABLE 1

| Score | Description |
| --- | --- |
| 0 | No evidence |
| 1 | Occasional evidence |
| 2 | Light scattering |
| 3 | Abundant evidence |
| 4 | Confluent cells |

Results

Several potential vehicles were screened for their biocompatibility. At processing the tissue for histology, an observation was made. For several animals, a void, suggesting that there was material present at the time that healing started, was noted. The observation was most consistent 2% alginate crosslinked with calcium (at all sites, in 4 of 6 sites with the magnesium crosslinked gel). These results in are shown in FIG. 1.

At a histological level, material was present in the majority of samples. The vehicle control showed some increase in inflammation compared to what is expected at this time point, perhaps due to low osmolality or pH. However, this was the buffer used for all formulations. The vehicles that showed the best biocompatibility (that is comparability with the control) were the alginates (cross linked with Calcium or Magnesium). The preferred vehicles from this screen were the alginate based vehicles. Results from these studies are shown in Tables 2-4.

TABLE 2

Scores for Sites Treated with 0.005M Phosphate Buffer pH 6.0

| Animal | Site | Score | | Comments |
| --- | --- | --- | --- | --- |
| 1-1 | L | 1 | 1 | 0 |
| 1-1 | R | 2 | 2 | 1 |
| 1-2 | R | 0 | 2 | 1 |
| 1-2 | L | 1 | 1 | 2 |
| 1-3 | R | 2 | 0 | 1 |
| 1-3 | L | 1 | 1 | 2 |

TABLE 3

Scores for Sites Treated with 2% Alginate crosslinked with 5 mM $Ca^{2+}$

| Animal | Site | Score | | Comments |
| --- | --- | --- | --- | --- |
| 7-1 | L | 2 | 2 | 1 | Material present microscopically |
| 7-1 | R | 1 | 0 | 2 | Material present microscopically and macroscopically |
| 7-2 | R | 1 | 2 | 2 | Material present microscopically |

TABLE 3-continued

Scores for Sites Treated with 2% Alginate crosslinked with 5 mM $Ca^{2+}$

| Animal | Site | Score | | | Comments |
|---|---|---|---|---|---|
| 7-2 | L | 1 | 2 | 1 | Material present microscopically and macroscopically |
| 7-3 | R | 2 | 0 | 0 | Material present microscopically and macroscopically |
| 7-3 | L | 1 | 2 | 2 | Material present microscopically |

TABLE 4

Scores for Sites Treated with 4% Alginate crosslinked with 50 mM $Mg^{2+}$

| Animal | Site | Score | | | Comments |
|---|---|---|---|---|---|
| 8-1 | L | 1 | 1 | 2 | Material present microscopically |
| 8-1 | R | 0 | 1 | 2 | Material present microscopically |
| 8-2 | R | 0 | 0 | 2 | Material present microscopically |
| 8-2 | L | 0 | 0 | 3 | Material present microscopically and macroscopically |
| 8-3 | R | 1 | 1 | 1 | Material present microscopically |
| 8-3 | L | 0 | 1 | 2 | Material present microscopically |

Example 2

Figure 2:
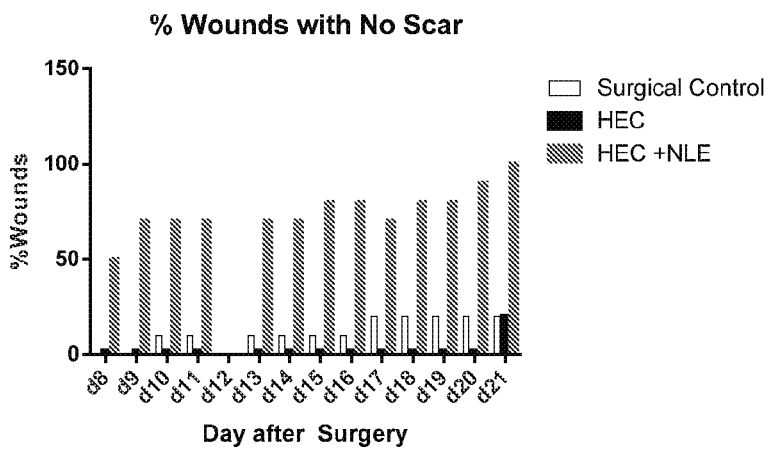
FIG. 2 is a graph showing the percent of treated wounds without scarring using different embodiments of the invention compared to control.
Figure 2:
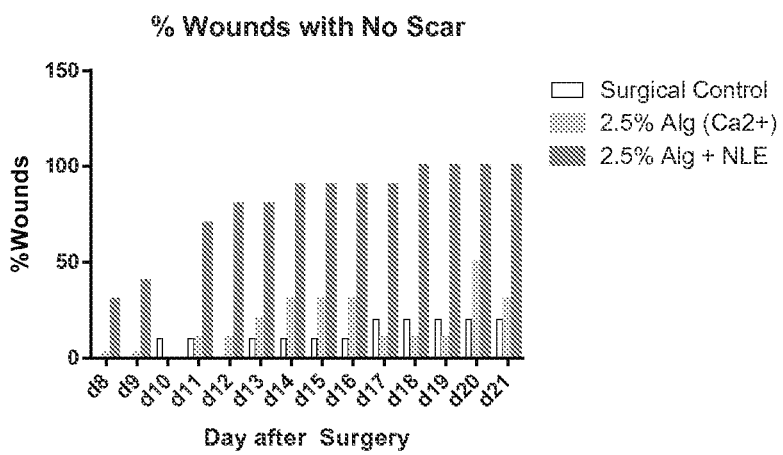
Figure 2:
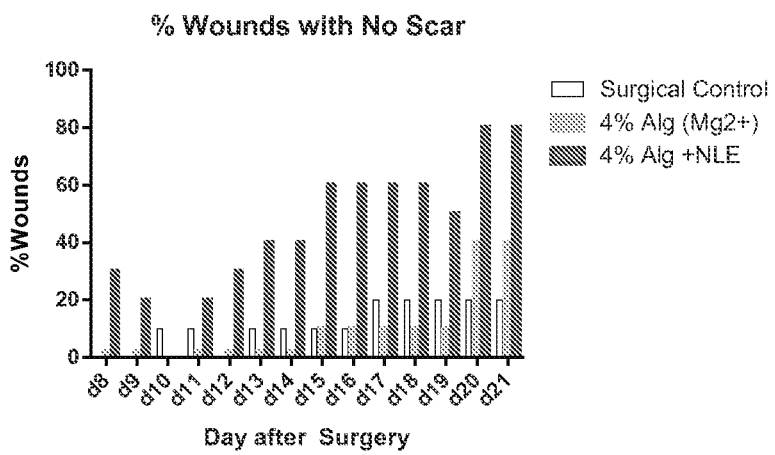

This example is designed to determine the formation and remodeling of scar by clinical and histological evaluations in full thickness incision wounds in a rat model. The vehicles that were tested include 2% HEC and two forms of cross-linked alginate.
Species:
  Sprague Dawley
  Female (n=5/group)
Parameters Measured: Appearance of Healing Wound (Gross and Histological)
Experimental Groups: Surgical control, 3 formulations with and without NorLeu$^3$-A(1-7) at 1 mg/ml)
Materials
  The hydroxyethyl cellulose formulation was provided by Adroit Pharmaceuticals and was used as provided. Alginate was supplied by FMC BioPolymer.
Formulations
  The alginate formulation was prepared by the following method. Sterile snap top polypropylene tubes (10×13 mm were pre-weighed and an aliquot of alginate added per tube. The tube was then post-weighed and the amount of diluent (0.005 M phosphate buffer) with and without NorLeu$^3$-A(1-7) added to make the percentage formulation listed. 5 mM $CaCl_2$ was added to 2.5% alginate or 50 mM $MgCl_2$ was added to 4% alginate to crosslink the alginate.
Surgical Model
  During the experimental period, Sprague Dawley rats, 200-225 grams, were housed one per cage and maintained in a central animal care facility with a 12-hour light/dark cycle. Water and standard rodent laboratory chow were supplied ad libitum. All animals used for this study received humane care as defined by the National Research Council's criteria for humane care. The study protocols were approved by the University of Southern California's Institutional Animal Care and Use Committee before initiation of the studies.
  Thirty five animals were placed in the study. Animals were necropsied at 21 days postoperatively. For each vehicle, five animals served as control and 5 were treated with 100 μg/wound of NorLeu3-A(1-7) in the vehicle. Two full thickness incisions (3 cm in length) were made on the surgically prepared dorsal surface of the rat under aseptic conditions. The wound was closed with interrupted sutures. One animal died from anesthesia during surgery (4% alginate with 50 mM $MgCl_2$ vehicle).
  The animals were monitored for breathing, urination and movement during the postoperative interval. Postoperative analgesia included twice-daily administration of bupronex for 3 days beginning on the day of surgery. During the first week after surgery, scabbing, dehiscence and inflammation were assessed. Daily starting in the second week after surgery (with the exception of weekends), the incisions were assessed for scar tissue by two trained individuals using the Hollander scale (see detail below). Each observer determined the scarring scale independently (the other observer was not in the room at the time of scar evaluation) at two separate settings allowing for calculation of inter and intra observer variation.
  On day 21 after surgery, the rats were euthanized by $CO_2$ asphyxiation and tissues harvested for histological preparation using hematoxylin and eosin stains as well as Masson's trichrome stain for collagen. Scar formation was assessed histologically. Histological observation included dermal architecture, collagen formation as well as reorganization and completeness of epidermal healing.
Observations on Unhealed Wounds
  The gross observations of the wound included:
  Inflammation
  Dehiscence (% of Incision Dehisced)
  Scabbing
  Inflammation and scabbing were assessed on a 4-point scale (0,1,2,3) for none, mild, moderate and severe, respectively. The gross evaluation of scar used the following scale:
  0 No observable by eye or feel
  1 Grossly visible, but thin. Slightly raised (may need ungloved hand to feel)
  2 Grossly visible, up to 1 mm line, Moderately raised line can be felt through glove
  3 Grossly visible, >1 mm wide, raising of the tissue evident by observation and touch, may have signs of inflammation
Quantitative Histomorphology
  Quantitative histomorphology was performed in each tissue section (cut at 10 mm intervals along the 3 cm length of the incision). Scar was defined as dermal tissue containing collagen (positive trichrome stain) arranged in a dense configuration. Analysis of the area of each tissue section was performed by normalizing the area of each tissue section by dividing the width of the incision (the height of the collagen in the reticular dermis). The scar area for a given animal was expressed as the summation of all area determinations divided by the number of tissue sections evaluated.
Results
  The data is summarized in FIG. 2. At early time points, scabbing and slight inflammation were noted in all groups, which is not unexpected due to the surgical procedure. All groups healed as expected. In the group treated with 4% alginate and 50 mM $Mg^{2+}$, there was slight erythema on days 8-9 with slight to moderate reddening in 2 or 5 animals. This resolved, but was not seen in the other groups, including that same formulation with NorLeu$^3$-A(1-7) included. While all vehicles delivered NorLeu$^3$-A(1-7) to reduce scar reduction, the most pronounced effects were seen with 2.5% Alginate with 5 mM $Ca^{2+}$, consistent with the prolonged release of NorLeu$^3$-A(1-7) seen in vitro with this vehicle compared to HEC control.

Example 3

This example was designed to determine the formation and remodeling of scar by clinical and histological evaluations in full thickness incision wounds in a rat model. Various doses of active ingredient were delivered in 2.5% alginate crosslinked with 5 mM $CaCl_2$.

Species:
 Sprague Dawley
 Female (n=5/group for histology; 3/group for tensile strength)

Parameters Measured:
 Appearance of Healing Wound (Gross and Histological of Dense Collagen by Image J)
 Tensile Strength
 Central, Blinded Adjudication of Photos on Day 21
 Photographic serial imaging Experimental Groups: Surgical control, vehicle (2.5% alginate crosslinked with 5 mM $CaCl_2$) and 2.5% alginate crosslinked with 5 mM $CaCl_2$ with 0.3, 1, 3 or 5 mg/ml DSC127)

Methods

Alginate was supplied by FMC BioPolymer. The alginate formulation was prepared by the following method. Sterile snap top polypropylene tubes (10×13 mm) were pre-weighed and an aliquot of alginate added per tube. The tube was then post-weighed and the amount of diluent (0.005 M phosphate buffer with various concentrations of DSC127) added to make the percentage formulation listed. 5 mM $CaCl_2$ was added to 2.5% alginate to crosslink the alginate.

Surgical Model

During the experimental period, Sprague Dawley rats, 200-225 grams, were housed one per cage and maintained in a central animal care facility with a 12-hour light/dark cycle. Water and standard rodent laboratory chow was supplied ad libitum. All animals used for this study were managed as per guidelines of Office of Animal Welfare as defined by the National Research Council's criteria for humane care. The study protocols were approved by the University of Southern California's Institutional Animal Care and Use Committee before initiation of the studies. Thirty animals were placed in the initial study (5/group). An additional 19 animals were place in a satellite study (3 in the surgical control group and 4/group in the alginate/peptide groups). Animals were euthanized at 21 days postoperatively. The six tests groups that were evaluated are: surgical control, vehicle control and 30, 100, 300 or 500 μg/wound of NorLeu3-A (1-7) in the vehicle. Two full thickness incisions (3 cm in length) were made on the surgically prepared dorsal surface of the rat under aseptic conditions for the main study. For the satellite study, one full thickness incision will be made on the surgically prepared dorsal surface of the rat. The wound was closed with interrupted sutures (4-0 Ethilon sutures, with a 19 mm, ⅜ c, reverse cutting multipass needle). The animals were monitored for breathing, urination and movement during the postoperative interval. Postoperative analgesia included twice-daily administration of bupronex for 3 days beginning on the day of surgery. During the first two weeks after surgery, scabbing, dehiscence and inflammation were assessed. Twice weekly starting in the second week after surgery the incisions were assessed for scar tissue by two trained individuals using the Hollander scale (see detail below). Each observer determined the scarring scale independently (the other observer was not in the room at the time of scar evaluation) at two separate settings on separate forms allowing for calculation of inter and intra observer variation. The observers had 2 years of animal handling experience and were trained on practice animals with scars to determine competency.

On days 21 after surgery, 5 rats were euthanized by $CO_2$ asphyxiation and tissues harvested for histological preparation using hematoxylin and eosin stains as well as Masson's trichrome stain for collagen. Scar formation was assessed histologically. Histological observation included dermal architecture, collagen formation as well as reorganization and completeness of epidermal healing.

Observations on Unheated Wounds

The gross observations of the wound included:
Inflammation
Dehiscence (% of Incision Dehisced)
Scabbing Scabbing was assessed on a 4-point scale (0,1,2,3) for none, mild, moderate and severe, respectively. Erythema was assessed on a 5 point scale as outlined below in Table 5.

TABLE 5

| Value | Erythema and Eschar Formation | Designation |
|---|---|---|
| 0 | No erythema | No erythema |
| 1 | Very slight erythema (barely perceptible, edges of area not well defined) | Very slight erythema |
| 2 | Slight erythema (pale red in color and edges definable) | Slight erythema |
| 3 | Moderate to severe erythema (definite red in color and area well defined) | Moderate erythema |
| 4 | Severe erythema (beet or crimson red) to slight escharformation (injuries in depth) | Severe erythema |

The percentage of the wound that has dehisced was calculated by dividing the length of the wound dehisced by the total length of the wound as measured using a plastic ruler. The gross evaluation of scar used the following scale:
 0 No observable by eye or feel
 1 Grossly visible, but thin. Slightly raised (may need ungloved hand to detect
 2 Grossly visible, up to 1 mm line, Moderately raised line can be felt through glove
 3 Grossly visible, >1 mm wide, raising of the tissue evident by observation and touch, may have signs of inflammation Quantitative Histomorphology Quantitative histomorphology was done in each tissue section (cut at 5 mm intervals along the 3 cm length of the incision) of the initial 5 animals per group. Scar was defined as dermal tissue containing collagen (positive trichrome stain) arranged in a dense configuration. Analysis of the area of each tissue section was done by normalizing the area of each tissue section by dividing the width of the incision (the height of the collagen in the reticular dermis). The scar area for a given animal was expressed as the summation of all area determinations divided by the number of tissue sections evaluated.

Tensile Strength

In a satellite study, additional animals with one incision per animal were entered into the study. Tissue thickness and width measurements as determined with a clear plastic ruler were recorded in order to normalize mechanical data to tissue thickness. Clamps used to secure the tissue were placed in the grips of an Instron Universal Testing Instrument. The Instron 5542 Biomaterials Testing equipment (Instron Corporation, Canton, Mass.) was then calibrated with the clamps in place. The tissue were inserted into the clamps 1 cm (parallel) from the incision line. Crosshead speed was set at 5 in/min. The tissue was tested in tension until failure. Tensile strength values were recorded and the site of rupture/tear was noted. All tissues that ruptured did so at the incision site. One tissue in the 5 mg/ml dose group did not rupture.

Results

Figure 3:
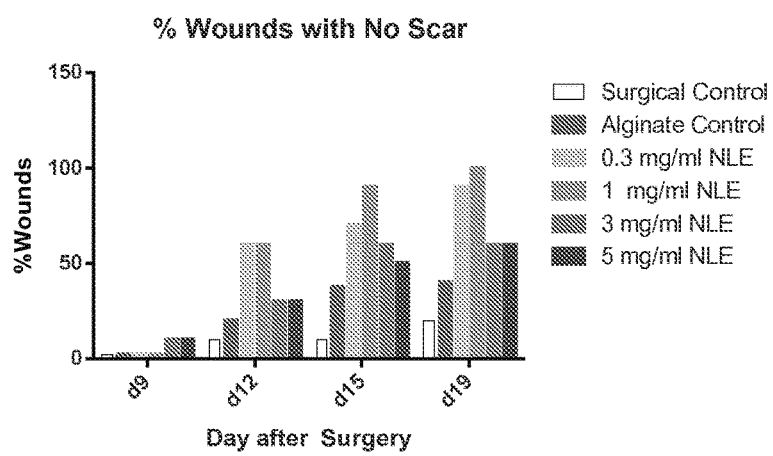
FIG. 3 is a graph showing the percent of treated wounds without scarring using different embodiments of the invention compared to control.

The wounds were assessed twice weekly after removal of the sutures at day 7 for appearance of scar. There was an early increase at day 12, in the number of wounds without apparent scar at the 0.3 and 1 mg/ml doses of NorLeu3-A (1-7) (NLE). This was not observed at day 12 with the two highest doses of NorLeu3-A(1-7), 3 and 5 mg/ml. See FIG. 3.

Figure 4:
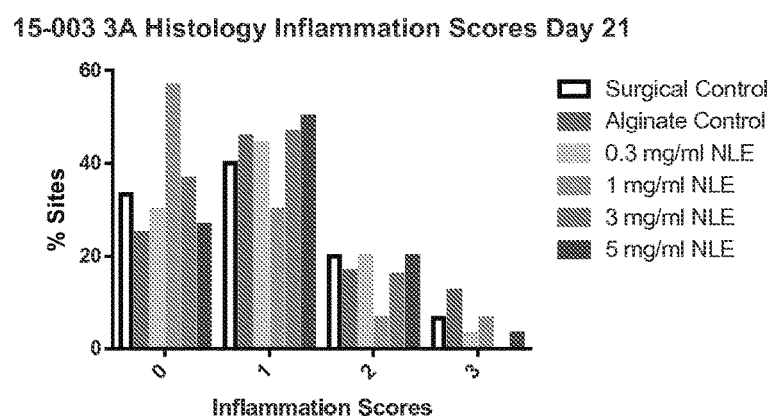
FIG. 4 is a graph showing histology inflammation scores using different embodiments of the invention compared to control.
Figure 5:
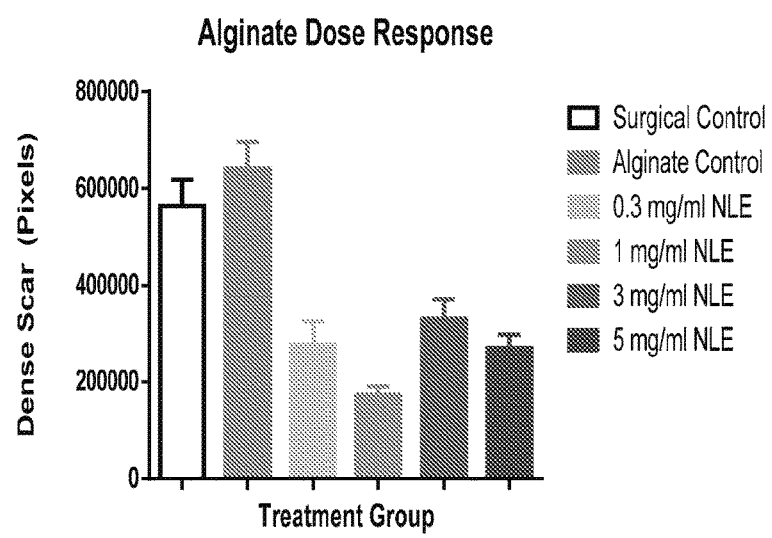
FIG. 5 is a graph showing alginate does-response studies using different embodiments of the invention compared to control.
Figure 6:
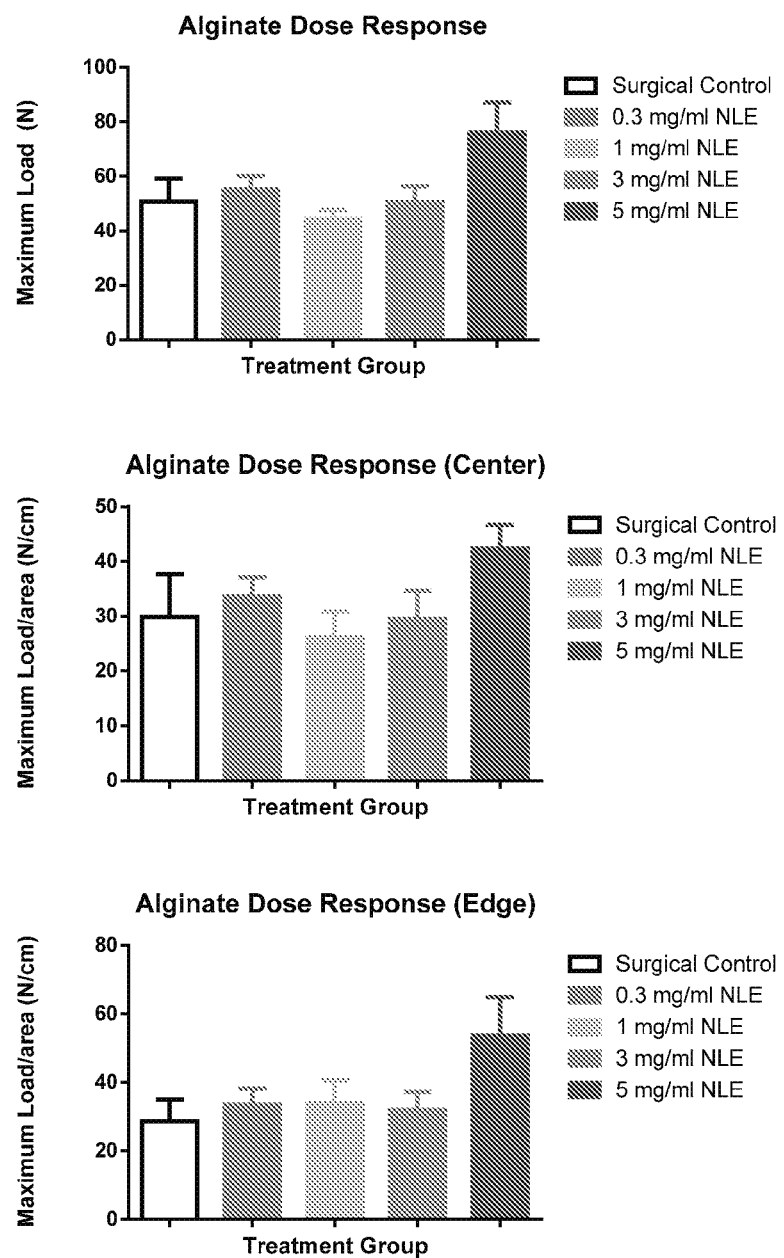
FIG. 6 is a graph showing alginate does-response studies using different embodiments of the invention compared to control.

Inflammation at the site of the incision was scored on histological sections at 3 levels for each incision. The distribution of score is seen on the graph to the right. There was no statistically significant differences between any groups, although there was a trend towards reduced inflammation compared with surgical and vehicle controls when 1 mg/ml NorLeu3-A(1-7) was included in the formulation. (FIG. 4) All doses of NorLeu3-A(1-7) in cross-linked alginate reduced the area of scar in the incision site (FIG. 5).

Satellite Study

In a satellite group of animals, the effect of placement of alginate formulations in the incision of the wound on the tensile strength of the incisional site was measured at day 21. There were no significant differences between groups on the measure of maximal load to cause rupture at the incision site or the maximal load per centimeter of tissue thickness. At the 5 mg/ml NorLeu3-A(1-7) dose, there was a trend towards an increase, with one of the 4 incisions tested.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

We claim:

1. A method for treating an incisional wound comprising: administering a composition comprising water, divalent ions, and alginate cross-linked by the divalent ions, into an incisional wound in a subject for a time and in an amount effective to treat the incisional wound, and closing the wound, wherein closing the wound comprises suturing or bonding the wound, wherein the suturing or bonding is carried out with the composition retained within the incision site.

2. The method of claim 1, wherein the incisional wound comprises an open surgical incisional wound or a trauma-induced incisional wound in the subject.

3. The method of claim 1, wherein the method reduces scar formation at the incisional wound, or reduces dehiscence following the closing of the wound, compared to control.

4. The method of claim 1, wherein the composition comprises between about 0.5% to about 10% alginate on a weight (mg)/volume (ml) basis, or on a weight/weight (mg) basis.

5. The method of claim 1, wherein the divalent ions comprise calcium ions at a concentration of between about 1 mM and about 10 mM.

6. The method of claim 1, wherein the divalent ions comprise magnesium ions at a concentration of between about 10 nM and about 100 mM.

7. The method of claim 1, wherein the alginate concentration is between about 2% and about 4% on a weight (mg)/volume (ml) basis, or on a weight/weight (mg) basis.

8. The method of claim 1, wherein the composition further comprises between about 0.001 M and about 0.010 M phosphate buffer.

9. The method of claim 1, wherein the composition further comprises a therapeutic agent.

10. The method of claim 9, wherein the therapeutic agent comprises a compound selected from the group consisting of peptides, proteins, antibodies, nucleic acids, and small molecules, or a combination thereof.

11. The method of claim 9, wherein the therapeutic agent comprises a peptide comprising the amino acid sequence of Nle3 A(1-7), or a pharmaceutically acceptable salt thereof.

12. The method of claim 11, wherein the composition comprises between about 0.001% to about 3% of Nle3 A(1-7), or a pharmaceutically acceptable salt thereof, on a weight (mg)/volume (ml) basis, or on a weight/weight (mg) basis.

13. The method of claim 1, wherein the alginate comprises 2% to 4% alginate on a weight (mg)/volume (ml) basis, or on a weight/weight (mg) basis.

14. The method of claim 13, wherein the divalent ions comprise about 5 mM $Ca^{2+}$ or about 50 mM $Mg^{2+}$.

15. The method of claim 13, wherein the composition further comprises about 0.005 M phosphate buffer.

16. The method of claim 1, wherein closing the wound comprises suturing the wound.

17. The method of claim 1, wherein closing the wound comprises bonding the wound.

* * * * *

SEQUENCE LISTING

<160> NUMBER OF SEQ ID NOS: 3

<210> SEQ ID NO 1
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is Nle

<400> SEQUENCE: 1

Asp Arg Xaa Tyr Ile His Pro
1               5

```
<210> SEQ ID NO 2
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is Nle

<400> SEQUENCE: 2

Asp Arg Xaa Tyr Ile
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is Nle

<400> SEQUENCE: 3

Asp Arg Xaa Tyr Ile His
1               5
```